(12) United States Patent
Khanna

(10) Patent No.: US 6,964,786 B1
(45) Date of Patent: Nov. 15, 2005

(54) **OIL FROM *MOMORDICA CHARANTIA L.*, ITS METHOD OF PREPARATION AND USES**

(76) Inventor: Pushpa Khanna, E-14/7, 1st Floor, Vasant Vihar, New Delhi 110 057 (IN)

( * ) Notice: Subject to any disclaimer, the term of this patent is extended or adjusted under 35 U.S.C. 154(b) by 0 days.

(21) Appl. No.: 10/031,288

(22) PCT Filed: Jul. 15, 1999

(86) PCT No.: PCT/IN99/00030

§ 371 (c)(1),
(2), (4) Date: May 9, 2002

(87) PCT Pub. No.: WO01/05416

PCT Pub. Date: Jan. 25, 2001

(51) Int. Cl.[7] .............................................. A61K 35/78
(52) U.S. Cl. ...................................................... 424/776
(58) Field of Search ........................................ 424/776

(56) References Cited

OTHER PUBLICATIONS http://rain-tree.com/bitmelon.htm Sep. 8, 2004.*

* cited by examiner

*Primary Examiner*—Herbert J. Lilling
(74) *Attorney, Agent, or Firm*—Morgan & Finnegan, L.L.P.

(57) ABSTRACT

The present invention relates to a novel oil extracted from the seeds of *Momordica charantia* L., for topical application to a body of mammal and used as anti-inflammatory, anti-arthritic, vasculodilatory and wound healing agent, said oil essentially comprising capric acid 0.7–1.2% by wt., lauric acid 0.6–1% by wt., palmitic acid 42–5.0% by wt., stearic acid 59–62% by wt., oleic acid 13–15% by wt., archid acid 3–5% by wt., linoleic acid 8–10% by wt., and other undetected minor acids 6–8% by wt.; and a process for producing such oil.

7 Claims, 3 Drawing Sheets

OIL FROM *MOMORDICA CHARANTIA L.*, ITS METHOD OF PREPARATION AND USES

FIELD OF THE INVENTION

The invention relates in general, to a novel oil extracted from the seeds of *Momordica charantia* L., (bitter gourd), its preparation and use as anti-inflammatory, anti-arthritic, vasculodilatory and wound healing agent.

BACKGROUND

The invention relates to a novel oil extracted from the seeds of *Momordica charantia* L., (bitter gourd). *Momordica charantia* is a perennial herb of the family Cucurbitaceae, widely grown in Asia. The herb is endemic to tropical countries like India, S. Africa, Philippines, China and Burma. The species of *Momordica* found in western countries are different from the tropical species in that, the plants differ in morphological and organoleptic properties. Various parts of this plant, especially the fruits, have been widely used for preparation of hypoglycemic pharmaceutical compositions.

The extract/juice of the fruit is known to exhibit hypoglycemic properties and often recommended to reduce the blood sugar levels in patients suffering from diabetes mellitus.

DESCRIPTION OF RELATED PRIOR ART

Natural oils from various plant sources have been used in variety of applications. For instance, U.S. Pat. No. 5,916,573 discloses grapeseed oil for tropical application on the skin. Similarly, U.S. Pat. No. 5,900,240 discloses herbal compositions and their use as hypoglycemic agents. The composition of this Patent comprises a mixture, of which the extract of *Momordica charantia* is one ingredient. This composition attends only to hypoglycemic conditions.

Various pharmaceutical compositions employing extracts from *Momordica charantia* are available in the market. However, most of these compositions are for oral administration and do not attend to the external manifestations and pathological conditions such as inflammations and wounds. Though, *Momordica* sp. has been the subject of extensive study all over the world, there is no literature on oil extracted from *Momordica charantia* L. In fact, there is a dearth of oil exhibiting anti-inflammatory, vasculodilatory, anti-arthritic properties in the market. As such, there is no report in literature on oil extracted from *Momordica charantia* L. In other words, the present invention is the first detailed study on Momordica oil and its properties.

OBJECTS OF THE INVENTION

It is an object of the invention to provide oil extracted from the seeds of *Momordica charantia* L. and a composition prepared therefrom.

Another object of the invention is to provide a method for the extraction of oil from the seeds *Momordica charantia* L.

Yet another object is to provide a method for the treatment of inflammations, wounds, arthritis, neuropathy developed due to diabetes mellitus and vasculodilatory conditions in humans and animals.

Still another object of the invention is to provide an oil composition comprising the oil from *Momordica charantia* L. mixed with any suitable pharmaceutically acceptable additives/carriers.

SUMMARY OF THE INVENTION

In accordance with the above and other objectives, the invention provides an oil composition prepared from the oil extracted from the seeds of *Momordica charantia* L., essentially comprising a mixture of Capric acid, Lauric acid, Palmitic acid, Stearic acid, Oleic acid, Archidic acid, Linoleic acid, other undetected minor acids and esters.

The invention also provides a process for the extraction of oil from the seeds of *Momordica charantia* L., using non-polar solvents.

Further, the invention teaches the use of the oily composition in the treatment of arthritis, diabetes and other conditions developed in diabetic patients.

DETAILED DESCRIPTION OF THE INVENTION

Accordingly, the invention provides oil extracted from the seeds of *Momordica charantia* L., essentially comprising:

| | | |
|---|---|---|
| 1. | Capric acid | 0.7–1.2% |
| 2. | Lauric acid | 0.6–1% |
| 3. | Palmitic acid | 4.2–5.0% |
| 4. | Stearic acid | 59–62% |
| 5. | Oleic acid | 13–15% |
| 6. | Archid acid | 3–5% |
| 7. | Linoleic acid | 8–10% |
| 8. | Other undetected minor acids | 6–8% |

Further, the invention provides a method for the extraction of oil from the seeds of *Momordica charantia* L., comprising the steps of:
 (i) grinding the dry seeds to a fine powder in a suitable mill,
 (ii) treating the pulverized seeds with a mixture of non-polar solvents,
 (iii) allowing the mixture to stand for 48 hours at room temperature so that the oil separates out,
 (iv) collecting the oil from the supernatant layer using a separatory funnel,
 (v) refluxing the mixture obtained in step (vi) with any non-polar solvent to remove the last traces of oil, and
 (vi) purification of the oil by precipitating the salts with impurities in it.

In one embodiment, the seeds of *Momordica charantia* L., are split, washed thoroughly with water, 2–3 times to render it substantially free from impurities and dried under vacuum, before using the seeds for extraction of the oil.

In another embodiment, the non-polar solvents used for extraction of oil may comprise a mixture of acetone with an aromatic or aliphatic hydrocarbon selected from the group of benzene, hexane, petroleum ether and ethyl ether.

In yet another embodiment, the ratio of acetone to the aliphatic or aromatic hydrocarbon in the non-polar solvent mixture may be 2:1.

In yet another feature, 2–5% zinc acetate dissolved in water may be used to precipitate the proteins and other impurities in the oil.

In another feature, the oil extracted is analyzed for its fatty acid contents using gas liquid chromatography (GLC).

It may be noted that most of the plant parts of *Momordica* contain the oil disclosed by the invention, in varying degrees. As such, the oil may be extracted using any plant parts preferably seeds.

A novel oil composition comprising oil extracted from the seeds of *Momordica charantia* L 70 to 80% by wt., one or more vegetable oils—15 to 25% by wt., fragrance oil —3% by wt, essential oil—1% by wt, and at least one perfume component—2% by wt.

In accordance with the present invention, the oil obtained from the seeds of *Momordica charantia* L., is thick reddish-orange in colour, having bitter taste. The oil extracted by the method described hereinabove is obtained in 98.5% purity. The oil is water immiscible. However, it is soluble in non-polar solvents like benzene, petroleum ether, ethyl ether, acetone and hexane.

The applicant through continued usage and after rigorous experimentation has found that the oil exhibits anti-inflammatory, anti-arthritic, vasulodilatory properties as it contains several unsaturated components like linoleic acid, oleic acid etc which are known for their antioxidant & anti-inflammatory properties.

It is found that the oil extracted from *Momordica charantia* L., is very thick and it is preferably used with diluents. Preferably, the oil may be mixed with other essential or vegetable oils. The essential oils that may be mixed with the oil from *Momordica charantia* could be selected from coconut oil, sesame oil, sunflower oil, olive oil, palm oil, groundnut oil or any such food grade oil. Further, it is found that when such food grade oils are mixed with the oils of Momordica, the penetration of the oil mixture into the outermost layers of the skin is enhanced to a great extent. The *Momordica* oil composition of the invention is prepared by mixing the 75% of the oil of *Momordica charantia* L., with vegetable oils selected from coconut oil, sesame oil sunflower oil, palm oil, olive oil or groundnut oil.

*Momordica charantia* oil composition may be prepared by mixing the oil extracted from *Momordica charantia* L, with vegetable oils and essential oils. The composition may also include, if desired, a botanical fragrance oil such as lavender oil, sandalwood oil, rose oil and geranium oils. The oil composition may further include a perfume component or other pharmaceutically acceptable additives. The oil composition is generally in the form of oil, cream, lotion, gel, capsule, suspension, solutions, or emulsion or a combination thereof, though the formulation is not limited to these forms. The oil composition of the invention, the oil extracted from *Momordica charantia* is thoroughly mixed and stirred with the essential oils at room temperature for 12 hours. The remaining components such as fragrance oil, perfume component or other additions are then added to the composition and vortexed for 10 hours at room temperature. The oil composition is applied in an amount sufficient to cover the targeted area of the clean, dry skin, with the fingertips or a cotton swab. In regions where there is no external injury or wound, it is advisable to massage the region locally for a 1–2 minutes after application of the oil composition. The penetrating effect of the oil composition to the outermost layers of the skin may be further enhanced by the addition of little vitamin E or oil containing vitamin E.

Studies on the oil composition of the invention suggest that topical use of the oil composition is safe and effective. There are no side effects.

BRIEF DESCRIPTION OF THE ACCOMPANYING DRAWINGS

The accompanying drawings are photographs of the pathological conditions of patients and the improvements therein:—

Figure 1:
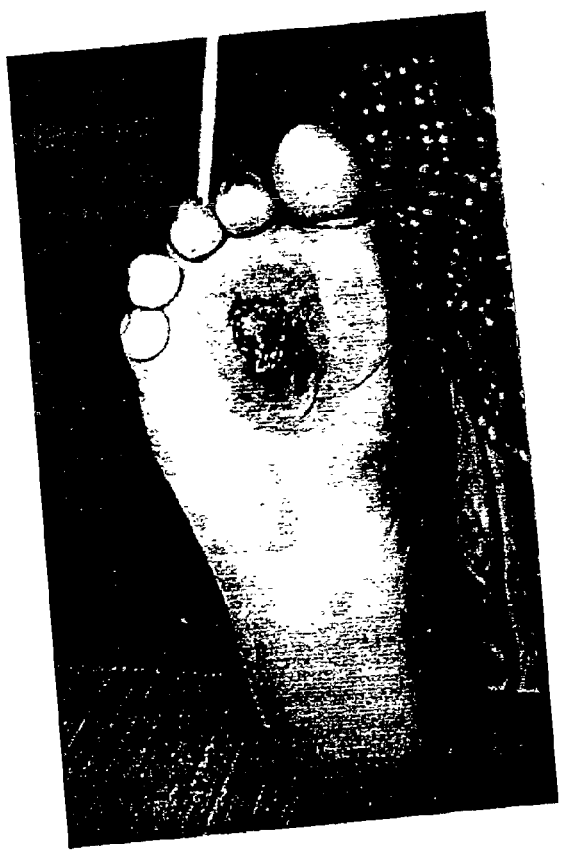
FIG. 1 represents the gangrenous wound on the sole of the right foot of the patient described in example No. 5, prior to the treatment.

The invention is described in detail with respect to the following examples which are provided as illustrative embodiments only. These examples should not be construed to limit the scope of the invention in any manner. Modifications and alterations of the invention that may be apparent to those in the art are deemed to be included within the scope of the invention.

EXAMPLE—1

Oil Preparative Example

Extraction of Oil from *Momordica charantia* L.:

100 gms of dry seeds were taken from the ripe fruits of *Momordica charantia* L.,. The seeds were split. The split seeds were then thoroughly washed with water 34 times to render them substantially free of all impurities. The seeds were then dried under vacuum and pulverized to a fine powder using a milling device. Any other conventional device may also be used. The fine powder was then treated with acetone hexane solvent mixed in the ratio 1:2. The mixture was stirred thoroughly and allowed to stand for 48 hours at room temperature. The oil layer was separated. The oil that separates out as supernatant layer was collected. The oil was then treated with 2–5% zinc acetate dissolved in water so that the salts, last traces of proteins and other impurities are precipitated. The oil was centrifuged and analyzed on gas-liquid chromatograph. The oil purified using gas liquid chromatograph showed the presence of the following fatty acids:

Capric acid 0.8%
Lauric acid 0.70%
Palmitic acid 4.8%
Stearic acid 60.3%
Oleic acid 13.0%
Archidic acid 3.0% and
Linoleic acid 10.0%

Other minor undetected components and acids 6.4%. The oil also contains esters and other undetected minor ingredients.

EXAMPLE 2

Extraction of Oil from *Momordica charantia* L.

200 gms of dry seeds were taken from the ripe fruits of *Momordica charantia* L.,. The seeds were split. The split seeds were then thoroughly washed with water 3–4 times to render them substantially free of all impurities. These seeds were then dried under vacuum and pulverized to a fine powder using a milling device.

Any other conventional devices may also be used. The fine powder was then treated with acetone benzene solvent mixed in the ratio 1:2. The mixture was stirred thoroughly and allowed to stand for 48 hours at room temperature. The oil in the supernatant layer was separated using a separatory funnel. The filtrate was refluxed with acetone-benzene and the process was repeated 2–3 times to separate out the last traces of oil. The oil that separates out as supernatant layer was collected. The oil was then treated with 2–5% zinc acetate dissolved in water so that the salts., last traces of proteins and other impurities are precipitated. The oil was centrifuged and analyzed on gas-liquid chromatograph.

The oil purified using gas liquid chromatograph showed the presence of the following fatty acids:

Capric acid 0.9%
Lauric acid 0.70%
Palmitic acid 4.8%
Stearic acid 60.1%
Oleic acid 13.81%
Archidic acid 3.28% and
Linoleic acid 10.00%
Other minor undetected acids 6.11%.

The oil also contains esters and other undetected minor ingredients.

EXAMPLE 3

Preparation of Oil Composition

The oil extracted from *Momordica charantia* L., as discussed in preparative examples 1–2 was kept in a beaker. Pure sesame oil was added to it in the ratio 3:1. The mixture was stirred continuously and thoroughly for 4–10 hours. Thereafter, fragrance oil like sandalwood oil as well as a perfume component were added to the mixture and stirred continuously and thoroughly for 4–10 hours. The formulation thus prepared stored in a container in a cool dry place.

The oil composition of the present invention can be formulated in a wide variety physical forms which include solutions, lotions, creams, oils, gels, sticks, sprays, ointments, balms, pastes, aerosols etc.

For preparation of an ointment, the active ingredients of the oil composition can be incorporated in any pharmacologically acceptable carrier, which is suitable for topical administration to the human skin. As such, the pharmacologically acceptable carrier must be of sufficient purity and have low toxicity to render it suitable for administration to a human. The carrier may represent a major portion of the total portion of the composition from at least 80%.

The composition of the invention may be formulated as a cream using a suitable carrier system.

A formulation may be prepared by introducing the oil composition into a lotion vehicle comprising glycerin, mineral oil, glycol stearate and other additives commonly known as Vasline Brand Intensive care lotion.

The following oil composition of the invention was prepared

Capric acid 0.9%
Lauric acid 0.8%
Palmitic acid 4.2%
Stearic acid 60.90%
Oleic acid 13.30%
Archidic acid 3.20% and
Linoleic acid 9.80%
Other minor undetected components and acids 6.90%

Creams, lotions, gels and other forms of the oil composition were made and tested as illustrated in the following examples:

Case Histories:

The following are examples of a series of confirmed cases of patients suffering from arthritis, diabetes, open wounds, inflammations etc. treated with the oil composition of the invention. Generally, the medication comprised tropical application of the oil composition (in various forms such as gels, lotions, suspensions, creams, etc.). The age group of these patients ranged from 30–80 years. The average duration of illness in the population was more than 5–6 years. All the patients prior to the treatment with the composition of the invention were using standard causes of therapy, exercise etc. Upon commencement with the oil composition as disclosed herein, the patients refrained from using other medications, except yoga and exercises. Specific excerpts from each case history is disclosed in the following examples.

EXAMPLE 4

A 30 year old Female working as a Receptionist had a bruise at her right elbow The oil composition was applied to the bruise caused at the elbow. The elbow was first cleaned and dried and the oil composition was applied slowly using a cotton swab. The oil composition was regularly applied after every 4 hours, for about 3–5 weeks. At the end of 15 days, the bruise healed completely.

EXAMPLE 5

Figure 2:
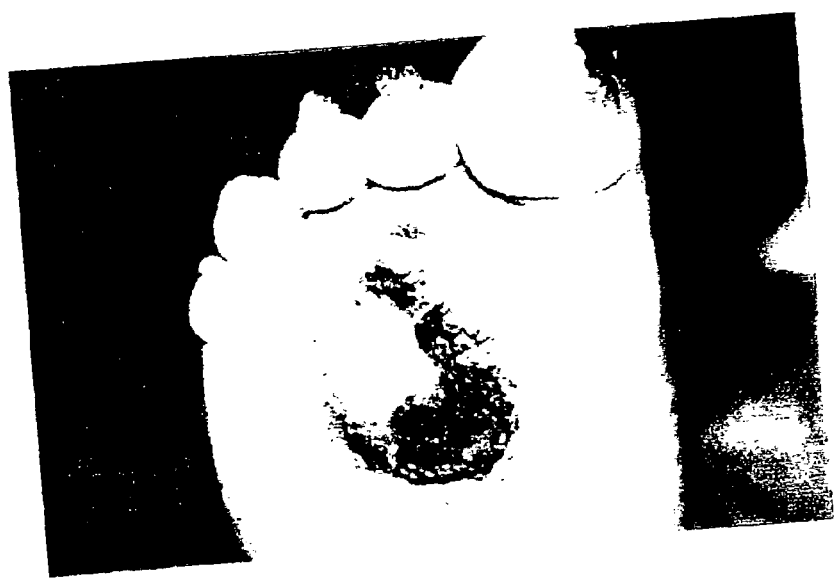
FIG. 2 represents the condition of the sole after two months of treatment with the oil composition of the invention.
Figure 3:
FIG. 3 represents the gangrenous wound on the left foot of the male patient in example No. 6 prior to the treatment.
Figure 4:
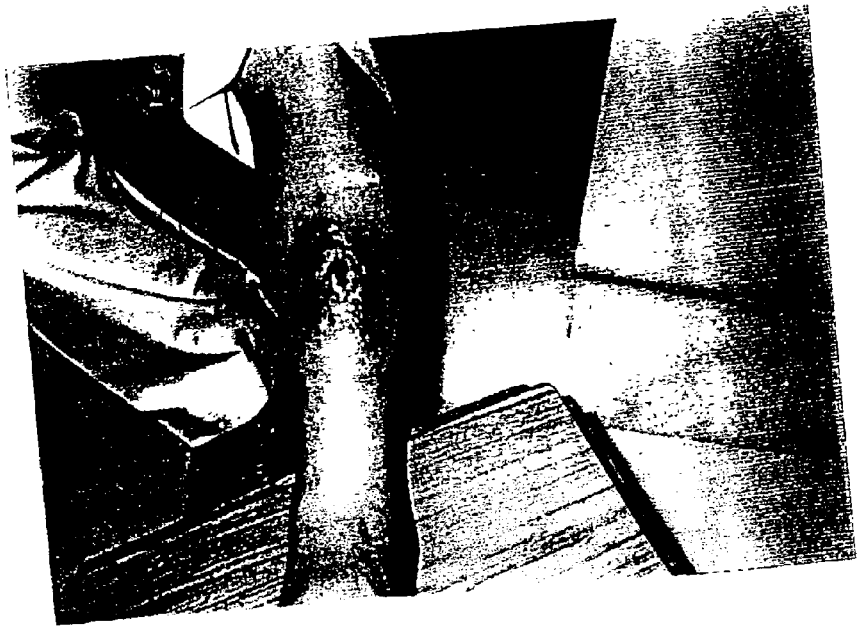
FIG. 4 represents the condition of the wound on the same patient one month after application of the oil composition of the invention.
Figure 5:
FIG. 5 represents the condition of the foot of the same patient two months after application of the oil composition of the invention.

The subject was a 65 year old male. This patient had a gangrenous wound on his right foot. The gangrene was in its advanced stages. It was a severe case of gangrene affliction. As there was no fresh blood supply, no healing constituted veins. The oil formulation of the invention was applied by the patient for about 10–12 weeks topically. After each application, the patient reported relief from the pain he suffered. At the end of the $6^{th}$ week itself, the wound started drying up and eventually after the 12 week the wound had healed completely. FIG. 1 depicts the gangrenous wound at the time of commencement of the treatment using the oil formulation of the invention. FIG. 2 shows the dried wound at the end of the $12^{th}$ week of the treatment.

EXAMPLE 6

A 45 year old female patient. This patient was chronic diabetic. She had a gangrenous wound on her left leg. The patient commenced application of the oil of the invention in the month of July 1997. After 1 month of usage, the patient found great relief. The wound had started showing signs of drying up and the patient also experienced relief from pain. At the end of 14 weeks itself, the wound had healed up completely and dried.

EXAMPLE 7

In one case, a 52 year old male had a leg ulcer, three to four inches in diameter. The ulceration was due to destruction of cellular components in the area. The patient was on standard medication. The patient cleaned the wound and applied the oil composition to the affected area daily every 4 hours. The treatment continued for 4 months. At the end of the second month, the wound had stinted drying up and showed signs of healing. After the third month, the healing was far advanced. By the end of the fourth month, the wound had healed completely and the tissues had commenced regeneration.

EXAMPLE 8

The next case involves a 53 year old market researcher based in Delhi, India, having a wet gangrene of the second toe with neurotic nail bed. The subject was unable to walk and was in great pain. He commenced usage of the oil composition of the invention, applying it about 3 times a day. The treatment continued for 2 months at the end of which, the nail, its bed as well as the toe had healed completely. After the third month, the subject had a normal toe.

EXAMPLE 9

A 35 year old male. Chartered Accountant suffered from osteoarthritis for more than 6 years. He complained of constant pain in the right knee and was unable to walk without a cane. His movements were restricted as the knee had become nearly stiff. Examination revealed that the synovial fluid had dried which lead to muscular tension. He had used oral drugs and pain killers, though of no avail.

This subject used the composition of the invention for about 3 months applying it continuously on the knee 3–4 times a day. After the first week the pain had reduced to a great extent. The subject was advised exercises to the extent possible. After 2 weeks, the patient could flex the knee to 45° with no pain. After 6 weeks, he could flex and rotate the knee in full range. He continued to apply the composition and after 8 weeks, was able to walk freely.

EXAMPLE 10

In another case, a housewife aged 52 years suffered from obesity. In addition, the patient complained of pain in the knee and ankle due to inflammation. The patient could hardly walk. She was using standard medication comprising drugs and injections, which did not help her much.

When the patient started using the composition of the invention, (application on the knee & ankle 4 times a day) she experienced relief in the dumb constant pain in the first week itself. After 2–3 weeks, she could stand and start walking to a limited extent. At the end of the $3^{rd}$ week, upward and downward movement at the ankle was possible. The knee was capable of flexing upto 45 degrees. After 8 weeks, the patient commenced regular walking, full movement/rotation of the knees and ankles.

EXAMPLE 11

A 32 year old female, working as a typist was suffering for more than a year, from spondylitis. The patient was advised to apply the oil composition of the invention regularly 3–4 times a day with massaging of the afflicted area. The medication gave her relief from pain in the $2^{nd}$ week itself. After 3–4 weeks, the patient could rescue neck movements. Full movements were observed after 12 weeks.

EXAMPLE 12

In one case, a female Laboratory Assistant aged 42 years had developed varicose vein. The native of her occupation required her to stand for long hours and she had the habit of wearing high heeled shoes. As a result, the leg muscles were stretched for long hours without relaxation. The entire body weight concentrated on her joints and ankles.

The stress caused capillaries to burst at the calf and blood that accumulated in the leg could be seen as blue spots and thick veins.

The Patient was recommended exercise and was advised to massage the oil composition of the invention at least 4 times a day. After 3 weeks, it was observed that the blue spots spread and after treatment for 10 weeks, the spots disappeared.

EXAMPLE 13

A 48 years old woman, working as an administrator in a firm, complained of osteoartritis. She had telescoping of the proximal interphalangeal joints of the left index finger. Minimal fusion was observed in the phalanges of both hands.

The patient was advised to apply the oil composition of the invention about 4 times a day, coupled with regular exercise. The patient reported relief from pain after 2 weeks, she reported restoration of function of both hands.

EXAMPLE 14

A manager aged 58 years, employed in a Bank, was suffering from diabetes mellitus. He also reported neuropathic symptoms with the rise in blood level. This patient was advised to apply the oil composition of the invention 4 times a day on his legs. He experienced relief and after 18 weeks reported complete relief from these symptoms.

EXAMPLE 15

A dog aged 3 years was wounded in a dog fight. The dog had a grievous wound on its left foreleg. The wound was about 1 cm in diameter and about ½ mm deep. The wound was cleaned and the oil composition of the invention was applied to it regularly after every 4 hours. After 10 days the wound started drying up giving rise to regeneration of tissues at the site of injury. After 30 days it was found that the wound had completely healed.

EXAMPLE 16

A horse aged 4 years was injured by a nail at the stable. The wound was 3 cm long and about ½ mm deep. This wound was cleaned thoroughly and the oil composition of the invention was applied to it nearly 3–4 times a day. After 10 days, sufficient amount of the tissue had grown over the wounded area and after 25 days, complete healing was observed.

The following is a table which gives the details of the patients treated using the oil composition of the invention:—

| S. No. | Sex of the patient treated | No of patients | Disease/pathological condition | General observations |
|---|---|---|---|---|
| 1. | Females | 85 | Gangrene | The oil composition of the invention was applied for about 25 weeks for complete healing. |
| 2. | Male | 125 | Gangrene | The oil composition of the invention was applied for about 20–30 weeks for complete healing. |
| 3. | Female | 32 | Spondylitis | The patients suffered spondylitis from the neck region and the lumbar region. Upon application of the oil composition for about 6–12 weeks, the |

-continued

| S. No. | Sex of the patient treated | No of patients | Disease/pathological condition | General observations |
|---|---|---|---|---|
| 4. | Male | 65 | Spondylitis | patients experienced relief and could resume normal functions. The patients suffered from pain in the neck, lumbar and lower back. Oil composition of the invention was applied for 6–15 weeks for complete relief. |
| 5. | Female | 63 | Rheumatoid arthritis | Patients suffered from pain in the joints. Oil composition of the invention was applied for 6–10 weeks for complete relief. |
| 6 | Male | 56 | Rheumatoid arthritis | Patients suffered from pain in the joints. Oil composition of the invention was applied for 6–12 weeks for complete relief. |
| 7 | Female | 45 | Neurophathic diabetes | Patients suffered from muscular pain in the legs and hands. The oil composition was applied for 15 weeks for complete relief. |
| 8 | Male | 73 | Neurophathic diabetes | Patients suffered from muscular pain in the legs and hands. The oil composition was applied for 15 weeks for complete relief. |

What is claimed is:

1. Oil extracted from the seeds of *Momordica charantia* L., useful as anti-inflammatory, anti-arthritic, vasculodilatory and wound healing agent, said oil comprising essentially of:

| | |
|---|---|
| Capric acid | 0.7–1.2% by wt. |
| Lauric acid | 0.6–1% by wt. |
| Palmitic acid | 4.2–5.0% by wt. |
| Stearic acid | 59–62% by wt. |
| Oleic acid | 13–15% by wt. |
| Archidic acid | 3–5% by wt. |
| Linoleic acid | 8–10% by wt. |
| Other undetected minor acids | 6–8% by wt. |

2. Oil as claimed in claim 1, comprising:

| | |
|---|---|
| Capric acid | 0.9% by wt. |
| Lauric acid | 0.8% by wt. |
| Palmitic acid | 4.2% by wt. |
| Stearic acid | 60.90% by wt. |
| Oleic acid | 13.30% by wt. |
| Archidic acid | 3.20% by wt. |
| Linoleic acid | 9.80% by wt. |
| Other undetected minor acids | 6.90% by wt. |

3. A process for preparing the oil of claim 1, comprising the steps of:
   (i) grinding dry seeds to a fine powder in a suitable mill,
   (ii) treating the pulverized seeds with a mixture of non-polar solvents,
   (iii) allowing the mixture to stand for 48 hours at room temperature so that the oil separates out,
   (iv) collecting the oil from the supernatant layer using a separating funnel,
   (v) refluxing the mixture obtained in step (iv) with any non-polar solvent to remove the last traces of oil,
   (vi) purifying the oil by adding 2–5% zinc acetate dissolved in water to precipitate the salts with impurities from the oil, and
   (vii) analysis of the oil extracted by gas liquid chromatography.

4. The process as claimed in claim 3 wherein the seeds of *Momordica charantia* L., are split, washed thoroughly with water 2–3 times to render the seeds substantially free from impurities and dried under vacuum before said grinding.

5. The process as claimed in claim 3 wherein the non-polar solvent comprises a mixture of acetone with an aromatic or aliphatic hydrocarbon selected from the group consisting of benzene, hexane, petroleum ether and ethyl ether.

6. The process as claimed in claim 5 wherein the ratio of the aliphatic or aromatic hydrocarbon in the non-polar solvent mixture is 2:1.

7. A method of treating a disease or condition in a patient body, comprising applying the oil of claim 1 or a composition comprising the oil of claim 1, on an affected area of the patient body for a period of about six to twenty weeks, wherein the disease or condition is selected from the group consisting of: inflammation, arthritis, vasculodilation and wounds.

\* \* \* \* \*